United States Patent
Corley, III et al.

(10) Patent No.: US 6,533,734 B1
(45) Date of Patent: Mar. 18, 2003

(54) TIME-INTEGRATED SAMPLER OF BODILY FLUID

(75) Inventors: Robert N. Corley, III, Tuskegee, AL (US); Michael R. Murphy; Samuel V. Panno, both of Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 0 days.

(21) Appl. No.: 09/591,570

(22) Filed: Jun. 9, 2000

Related U.S. Application Data
(60) Provisional application No. 60/138,907, filed on Jun. 11, 1999.

(51) Int. Cl.$^7$ ............................. A61B 5/00; B65D 81/00
(52) U.S. Cl. ..................... 600/573; 600/581; 119/174
(58) Field of Search .................... 600/573, 576, 600/579, 580, 581, 582; 604/22, 109, 19; 606/160; 119/14.19, 14.2, 174

(56) References Cited

U.S. PATENT DOCUMENTS

| | | | |
|---|---|---|---|
| 3,570,498 A | * 3/1971 | Weighton | .................. 604/109 |
| 3,653,359 A | * 4/1972 | Tolle et al. | .............. 119/14.02 |
| 4,036,214 A | 7/1977 | Bucalo | |
| 4,325,388 A | 4/1982 | Bucalo | |
| 4,590,165 A | * 5/1986 | Gilles et al. | .................. 436/49 |
| 5,325,867 A | 7/1994 | Skrabal et al. | |
| 5,678,564 A | * 10/1997 | Lawrence et al. | .......... 600/574 |
| 5,817,007 A | * 10/1998 | Fodgaard et al. | .......... 600/322 |
| 5,851,985 A | * 12/1998 | Tepic et al. | ..................... 514/2 |
| 6,129,680 A | * 10/2000 | Mottram | .................... 600/532 |
| 6,241,688 B1 | * 6/2001 | Bouda et al. | ............... 600/573 |
| 6,251,394 B1 | * 6/2001 | Nilsson et al. | ........... 424/140.1 |

OTHER PUBLICATIONS

University of Guelph, ADSA '97 Programs and Abstracts, Journal of Dairy Science, vol. 80, Suppl. 1, 1997, p. 260, P450.
Abstract of Soviet Union Patent No. SU 1012894 A filed Apr. 23, 1983.
Abstract of Soviet Union Patent No. SU 1060173 A filed Dec. 15, 1983.
Abstract of article: Huhtanen,–P; Brotz,–P.G.; Satter,–L.D entitled "Omasal sampling technique for assessing fermentative digestion in the forestomach of dairy cows" from J–anim–sci Champaign Ill.: American Society of Animal Science May 1997, vol. 75(5) p. 1380–1392.
Abstract of article: Rogers–W.R; Lucas–J.H; Mikiten–B.C.; Smith–H.D.; Orr–J.L. entitled "Chronically indwelling venous cannula and automatic blood sampling system for use with nonhuman primates exposed to 60 Hz electric and magnetic fields" from Bioelectromagnetics 0(SUPPL.3): 103–110; 1995.

(List continued on next page.)

*Primary Examiner*—Kevin Shaver
*Assistant Examiner*—Charles Marmor, II
(74) *Attorney, Agent, or Firm*—Polit & Associates, LLC

(57) ABSTRACT

An apparatus and corresponding method obtains time-integrated samples of fluid from the rumens of cattle, sheep, goats or other animals through a cannula. The apparatus allows ruminal fluid to be sampled under standard conditions. It reduces the labor required to obtain samples and allows dynamic fermentation patterns to be followed. The apparatus includes a ceramic filter connected to a sampling tube assembly. The filter is placed in the rumen and vented to atmosphere by a first tube. A second tube connects an inside region of the filter to a peristaltic pump which removes fluid for time-integrated sampling.

20 Claims, 2 Drawing Sheets

OTHER PUBLICATIONS

Abstract of article: Clark–R.G.; Chambers–G; Lewin–J; Robinson–I–C–A–F entitled "Automated repetitive microsampling of blood: Growth hormone profiles in conscious male rats" from Journal of Endocrinology 111(1):27–36.

Abstract of article: Oliveira Mds–de; Sampaio–Aam; Vieira–P–de–F; Banzatto–Da; De–Oliveira–Mds; DeFigueiredo–Vieira–P entitled "Digestibility of DM, crude protein and gross energy of maize silage and concentrate mixtures estimated in vivo and in vitro" from Rivsta–Brasileira–de–Zootecnia. 1997, 26:3, 590–594; 8 ref.

Abstract of thesis: Wagner–D entitled "Comparative evaluation in adult cattle of 4 rumen fluid sampling instruments with regard to contamination of the samples with saliva" Universitat Munchen; German Federal Republic 1984, 101 pp.; 82 ref.

P. Huhtanen, P.G. Brotz, and L.D. Satter entitled "Omasal Sampling Technique for Assessing Fermentative Digestion in the Forestomach of Dairy Cows" from the Journal of Animal Science, vol. 75, May 1997 pp. 1380–92.

Sorenson, V. and P. Schanbye, Apparat zur entnahme von panseninhalt (dänish), 1955, Medl. Danske Vet. Foren. 38:60.

* cited by examiner

TIME-INTEGRATED SAMPLER OF BODILY FLUID

This patent application claims the benefit of provisional application U.S. Ser. No. 60/138,907 filed Jun. 11, 1999.

The invention was made with Government support and the Government has certain rights in the invention.

TECHNICAL FIELD OF THE INVENTION

The invention relates to fluid sampling in living creatures. Particularly, the invention relates to sampling of fluid from the rumens of cattle, sheep, or goats.

BACKGROUND OF THE INVENTION

Unlike nonruminants (e.g., horses, poultry and swine), ruminants (e.g., cattle, goats and sheep) have a four-compartment stomach. The rumen is the largest compartment and functions as a large fermentation chamber, in which microbes produce volatile fatty acids. These are then absorbed and used by the animal for productive purposes (e.g., milk production and growth). The importance of volatile fatty acids to animal-productivity has resulted in the development of frequent and labor-intensive sampling methods for their determination.

Researchers, large feed companies, and some private laboratories devote considerable resources to measuring the effects of various feeds and feed treatments on ruminal fermentation. The pattern of fermentation in the rumen must be closely monitored using some sort of sampling apparatus to properly determine the nutritional value of diets. Fermentation in the rumen [e.g., the production of volatile fatty acids (acetic, propionic, butyric, and higher acids)] is a dynamic process and a major determinant of the efficiency of animal growth, milk production, and milk composition.

Ruminal sampling methods also are important in veterinary practice. These techniques are responsible for assisting in the diagnosis of digestive diseases and latent or clinical conditions affecting digestion and the well-being of the animal. A critical factor limiting our ability to gather data about ruminal fermentation has been the lack of appropriate sampling methods.

Several factors complicate ruminal sampling; however, most arise from the heterogeneous nature of the ruminal contents and the dynamics of the digestion process. A sample representative of the biological and biochemical environment of the rumen is best collected under standard conditions in relation to time of feeding and location in the rumen, preferably from the center or ventral ruminal sac. Ruminal fluid samples should also be taken over time to account for diurnal changes.

Conventional methods of collecting ruminal fluid may not produce representative samples in terms of quality and quantity, while methods able to provide representative samples are often impractical. The various approaches currently used to obtain samples of ruminal fluid are:

A. Slaughter

1. Description

Digesta fluid samples have been obtained at slaughter for many years [e.g., Ulyatt, M. J. et al. 1984. Effect of intake and feeding frequency behavior and quantitative aspects of digestion in sheep fed chaffed lucerne hay. J. Agr. Sci. (Camb.): 102:645]. The technique has proved most useful for sampling digesta fluid in wild animals, although occasionally it has been employed in agricultural studies.

2. Problems a. The main disadvantage of sampling at slaughter is that only single samples are obtained. Rarely does such a sampling scheme fit into current experiments on valuable livestock or endangered animals. It has been used recently only in very intensive experiments with few animals. Even more rarely is it used with wild animals.

b. Standard technique also requires that feed be withheld from animals for some interval before slaughter. This artificial situation makes the samples obtained less valuable. Special arrangements have sometimes been made at slaughter to allow rapid sampling after exsanguination.

c. Digestion is dynamic; therefore, several samples should be collected over the day to adequately describe the process. This problem has been handled by slaughtering groups of animals at various times after feeding; however, it is obviously a costly and time-consuming approach.

B. Stomach Tube

1. Description

In this technique, digesta fluid samples are obtained by aspiration through a tube passed through a speculum in the mouth and via the esophagus to the reticulorumen of intact animals (e.g., Geishauser, T., and A. Gitzel. 1996. A comparison of rumen fluid sampled by ororuminal probe versus rumen fistula. Small Ruminant Res. 21:63; and Dirksen, G., and M. C. Smith. 1987. Acquisition and analysis of bovine rumen fluid. Bovine Pract. 22:108).

2. Problems a. A major problem with this technique is that the fluid samples obtained are often contaminated with variable quantities of saliva and mucus. Some have tried to reduce the problem by discarding the first part of the sample obtained by aspiration.

b. The position of the sampling tube in the reticulorumen is unknown during sampling. The composition of spot samples from various locations in the reticulorumen often differs; therefore, it is unlikely that fluid samples via a stomach tube are representative of the overall environment in the reticulorumen.

This problem has been handled by focusing on differences between treatments so that the results obtained are not considered quantitative measures of the overall environment in the reticulorumen.

c. Animals must be disturbed and additional restraint applied to effectively sample with this method. This is especially problematic when repeated sampling is required. This problem has been handled by avoiding repeated sampling and developing skilled handlers who can obtain samples while minimizing disturbance of the animal.

d. Repeated sampling increases the labor required to obtain samples. This drawback has been recognized by all who have been involved in 24-hour sampling protocols. It is usually handled by enlisting groups of people to cooperate during sampling periods.

e. The sampling tube is often plugged when vacuum is applied because large digesta particles occlude the holes through which fluid would otherwise move. This problem occurs frequently and is usually overcome by sliding the sampling tube in and out to scrape off particles blocking the holes.

C. Naso-ruminal Sampler

1. Description

A naso-ruminal sampler obtains digesta fluid by aspiration through an indwelling tube passed through the nose and pharynx and then via the esophagus to the recitulorumen of intact animals [e.g., Poulsen, S. D. et al. 1988. Clinical chemical comparative examination or ruminal samples collected by means of a naso-ruminal sampler. Acta. Vet. Scand. 29:129; and Moloney, A. P. 1997. Comparison of procedures for the collection of rumen fluid from cattle. Irish J. Ag. Fd. Res. 36(Suppl. 1): 108 (Abstr.)].

2. Problems a. Naso-rumen samples of digesta fluid would not be representative of the overall environment of the reticulorumen, because fluid is obtained from a single but unknown location. As with the samples obtained using a stomach tube, the problem has been handled by focusing on differences between treatments so that the results obtained are not considered quantitative measures of the overall environment in the reticulorumen.

b. Animals must be disturbed and additional restraint applied to effectively sample with this method. This is especially problematic when repeated sampling is required. This problem has been handled by avoiding repeated sampling and developing skilled handlers who can obtain samples while minimizing disturbance of the animal.

c. Repeated sampling increases the labor required to obtain samples. This drawback has been recognized by all who have been involved in 24-hour sampling protocols. It is usually handled by enlisting groups of people to cooperated during sampling periods.

d. The sampling tube is often plugged when vacuum is applied because large digesta particles occlude the holes through which fluid would otherwise move. This problem occurs frequently and is usually overcome by sliding the sampling tube in and out to scrape off particles blocking the holes.

D. Spot Sampler

1. Description

This technique utilizes an evacuated flask to obtain composite samples of digesta fluid from several sites via a perforated tube in cannulated animals (e.g., Woodford, S. T., and M. R. Murphy. 1988. Dietary alteration of particle breakdown and passage from the rumen in lactating diary cattle. J. Dairy Sci. 71:687). This method is the most common currently employed. A ruminally cannulated animal is required.

2. Problems a. Frequent and labor-intensive sampling is required to adequately describe the dynamics of digestion. This drawback has been recognized by all who have been involved in 24-hour sampling protocols. It is usually handled by enlisting groups of people to cooperate during sampling periods.

b. Repeated removal and replacement of the cannula cover disturbs the animal and may allow digesta to escape. This seems to be an unaddressed problem with the spot-sampling method.

c. The sampling tube is often plugged when the vacuum is applied because large digesta particles plug the holes through which fluid would otherwise move. This problem occurs frequently and is usually overcome by sliding the sampling tube in and out to scrape off the particles blocking the holes.

E. Rumenocentesis

1. Description

Herd health is sometimes monitored by sampling digesta fluid from the outside of selected intact animals using a needle attached to a syringe to penetrate the reticulorumen (e.g., Nordlund, K. V., and E. F. Garrett 1994. Rumenocentesis: a technique for collecting rumen fluid for the diagnosis of subacute rumen acidosis in diary herds. Bovine Pract. 28:109). The technique is usually employed to determine the pH of digesta in the reticulorumen. A low pH is interpreted to indicate the possible presence of acidosis or subclinical acidosis.

2. Problems a. Animals must be disturbed and additional restraint applied to effectively sample with this method. It is also problematic when repeated sampling is required. This problem seems unavoidable when rumenocentesis is employed. Animal health and welfare concerns would seem to preclude repeated sampling with this method.

b. A small sample volume (1 to 3 ml) is obtained. This problem limits the analyses that can be conducted and, as a spot sample, is not representative of the overall ruminal environment. The proposed method allows collection of about 55 ml per hour, an adequate but not excessive sampling rate.

c. There is potential for inflammatory reaction at site of needle entry. Pathogen entry is always a risk in surgical procedures and aseptic methods are recommended for rumenocentesis.

d. At best, this technique (as currently employed) is of questionable value in describing the dynamics of digestion. Use of rumenocentesis to sample digesta fluids and interpretation of its results is currently a controversial topic in ruminant nutrition and veterinary medicine.

SUMMARY OF THE INVENTION

The invention provides an apparatus and method for sampling body fluids from an animal body, including from humans, using a filter to be inserted into the body and a first tube venting the filter to atmosphere and a second tube extending from inside the filter to outside the animal body. A pump draws sampled fluid which collects inside the filter, to a collection vessel.

This invention includes an apparatus and method that allows time-integrated and representative samples of ruminal fluid to be obtained with less error and labor. The apparatus includes a cup shaped ceramic filter located within the rumen of the animal. The filter is vented to remain at atmospheric pressure. A draw tube removes fluid which flows into the filter via a peristaltic pump.

The time-integrated sampler can comprise a small cup-shaped ceramic filter, two outer tube lengths connected at an angle, one inner flexible tube and one outer flexible tube, a ruminal cannula cover, and a peristaltic pump. The filter connects to the outer flexible tube via a clamp. The neck of the filter can extend close to the end of the outer tube lengths. The outer flexible tube is tethered outside the rumen to prevent it from being moved during ruminal contractions. The outer tube lengths extend from the filter through the cannula cover or plug and maintain the filter in the ventral rumen while securing the outer flexible tube. Thus, the filter is inserted into the ventral rumen by closing or replacing the cannula cover. This allows the filter to be easily removed for cleaning and inspection.

The inner flexible tube, through which filtrate entering the filter is removed continuously, travels from the inside base of the filter through the outer flexible tube and, via a peristaltic pump, into a collection vessel. The inner flexible tube can be kept in place using small clamps inside the outer flexible tube. It is important to note that the peristaltic pump is not responsible for the flow of fluid into the filter but for removing fluid that passively enters the filter. Ruminal fluid flows into the filter due to the natural pressure gradient existing in the ventral rumen and not because of an external source of vacuum.

A time-integrated, therefore, representative sample relying on natural mixing contractions is achieved. Repeated sampling is possible, therefore the diurnal dynamics of fermentation can be followed. Fixed, known, optimal sampling position is achieved. The sampling rate is adequate to support varied and repeated chemical analyses, but not so fast that the dynamics of ruminal fermentation are adversely affected.

Reduced sample processing is achieved. Most particles are removed as fluid seeps into the filter with 6-$\mu$m pores; therefore, the usual filtering step is avoided saving materials and labor. Reduced or eliminated clogging of the tube during sampling is achieved. Manipulation of the device is not required to obtain continuous or repeated samples.

The device and method are adaptable to automatic sampling. By coupling the peristaltic pump to a fraction collector, composite samples integrated over arbitrary time periods could be obtained automatically. This provides a significant labor savings. The device and method are adaptable to ambulatory or remote sampling. Ambulatory and remote sampling of ruminal fluid would be valuable in situations in which animals are not confined, e.g., grazing.

The method provides a labor savings. The device has a relatively simple construction.

A small dead volume allows rapid stopping of fermentation and less exposure to air than all techniques, except rumenocentesis.

Numerous other advantages and features of the present invention will become readily apparent from the following detailed description of the invention and the embodiments thereof, from the claims and from the accompanying drawings.

DETAILED DESCRIPTION OF THE PREFERRED EMBODIMENTS

Figure 1:
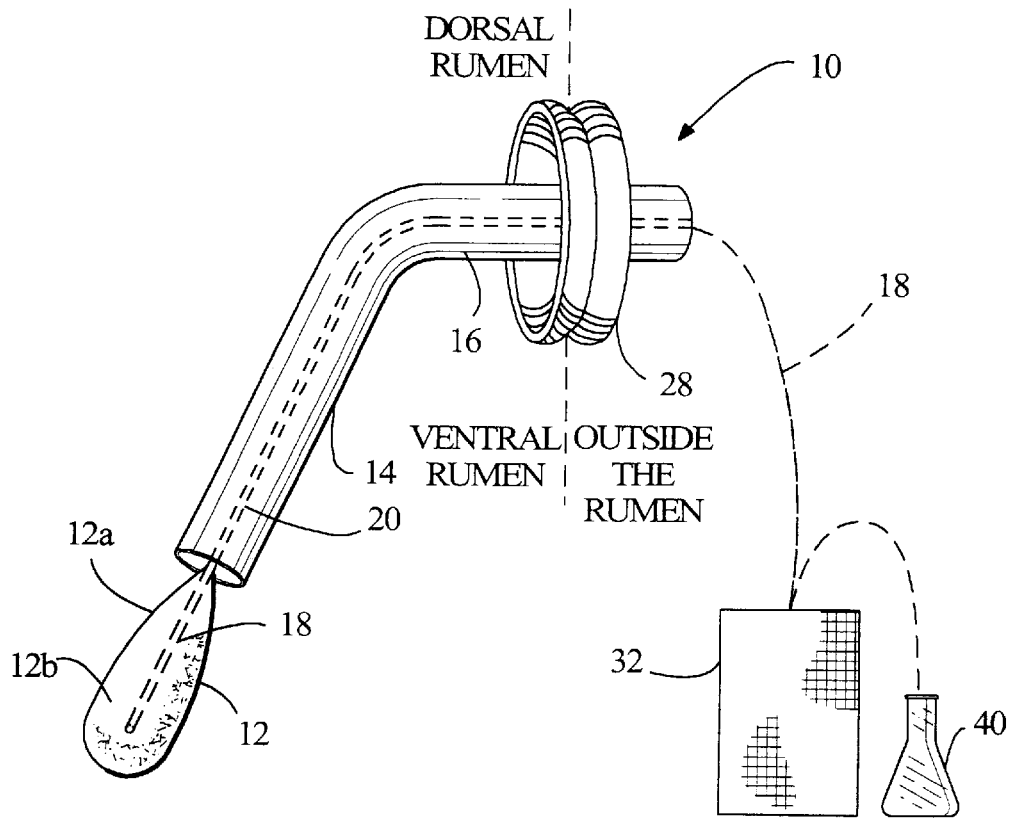
FIG. 1 is a schematic view of a sampling system of the present invention.
Figure 2:
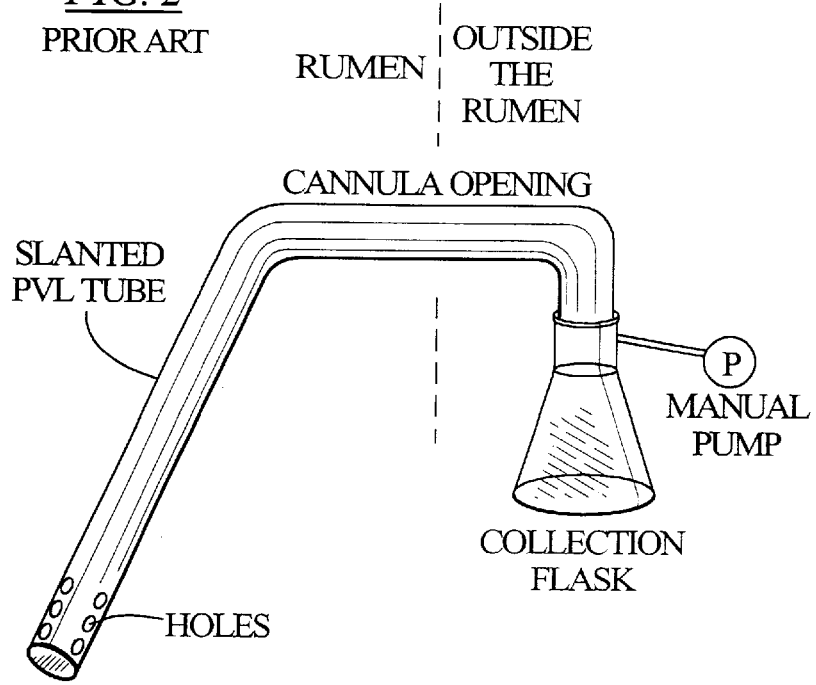
FIG. 2 is a schematic view of a prior art sampling system.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

FIG. 1 illustrates a time-integrated sampler 10 that comprises a small cup-shaped ceramic filter 12 (such as manufactured by Soil Moisture Equipment Corp., Santa Barbara, Calif.), two outer tube lengths 14, 16 (polyvinyl chloride (PVC), preferably 50 cm long with a diameter of 2 cm) connected at an angle, one inner flexible tube 18 (preferably plastic) and one outer flexible tube 20 (preferably plastic), a ruminal cannula cover 28 and a peristaltic pump 32 (such as manufactured by Rabbit, Rainin Instrument Co., Woburn, Mass.). The filter 12 connects to the outer flexible tube 20 via a clamp (not shown). A neck 12a of the filter 12 can extend close to the end of the outer tube length 14. The outer flexible tube 20 is tethered outside the rumen to prevent it from being moved during ruminal contractions. The outer tube lengths 14, 16 extend from the filter through the cannula cover and maintains the filter in the ventral rumen while securing the outer flexible tube 20. Thus, the filter can be inserted into the ventral rumen by closing or replacing the cannula cover 28. This allows the filter to be easily installed and removed for cleaning and inspection.

The inner flexible tube 18, through which filtrate entering the filter is removed continuously, extends from the inside base 12b of the filter 12 through the outer flexible tube 20 and via the peristaltic pump 32 into a collection vessel 40. The inner flexible tube 18 can be kept in place using small clamps (not shown) inside the outer flexible tube 20.

It is important to note that the peristaltic pump 32 is not responsible for the flow of fluid into the filter but for removing fluid that passively enters the filter. Ruminal fluid flows into the filter 12 due to the natural pressure gradient existing in the ventral rumen and not because of an external source of vacuum.

Figure 3:
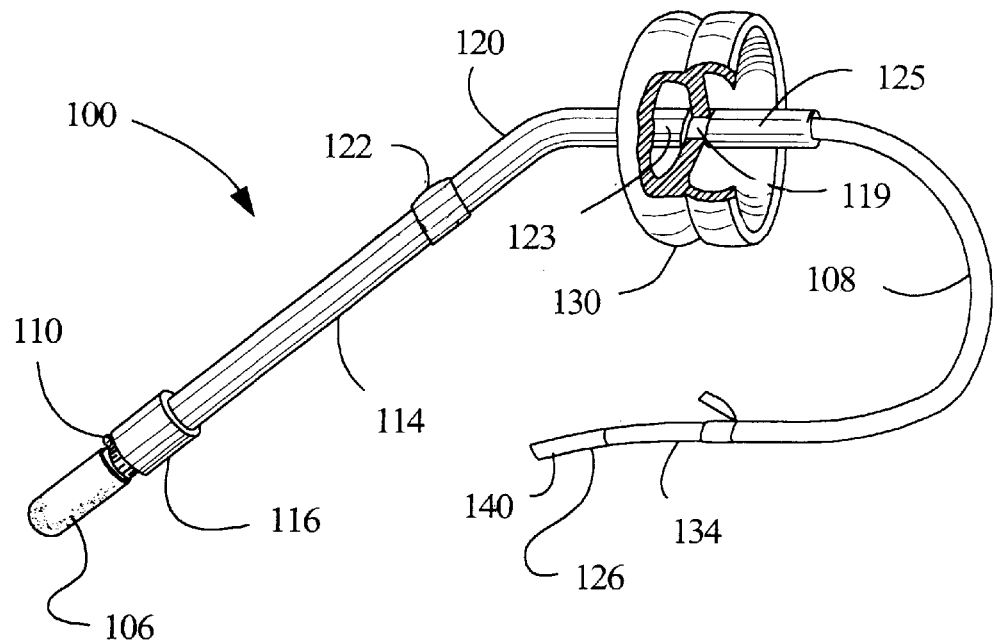
FIG. 3 is a perspective view of the apparatus of the present invention.

FIG. 3 illustrates a preferred embodiment sampling device 100. The sampling device includes a cup-shaped ceramic filter 106 which is connected to an outer flexible tube 108, preferably plastic, via a screw activated clamp 110. An outer sleeve 114, preferably a PVC tube, surrounds the outer flexible tube 108. The sleeve 114 is connected to a 45° elbow 120 by a coupling 122. The elbow 120 is connected to a further coupling 123 which connects a short straight section 119 to a further coupling 125. The couplings 123, 125 capture a cannula plug 130 therebetween, to fix the cannula plug or cover 130 onto the short straight section 119.

The outer flexible tube 108 extends from an open end 134, through the coupling 125, through the short straight section 119, through the coupling 123, through the elbow 120, through the coupling 122, through the sleeve 114, through a coupling 116, to the clamp 110, to be connected to the ceramic filter 106. The ceramic filter is thus vented to atmospheric pressure through the outer flexible tube 108 which extends outside the rumen through the cannula plug 130. Inserted through the outer flexible tube 108, is an inner flexible tube 126, preferably plastic, which extends through the open end 134 of the outer flexible tube 108 to the ceramic filter 106. The inner flexible tube 126, as shown schematically in FIG. 1, extends into the ceramic filter and has a hole or open end 126a (FIG. 4) therein to receive fluid from the rumen. The opposite end 140 of the inner flexible tube 126 is connected to a peristaltic pump as described in FIG. 1.

Figure 4:
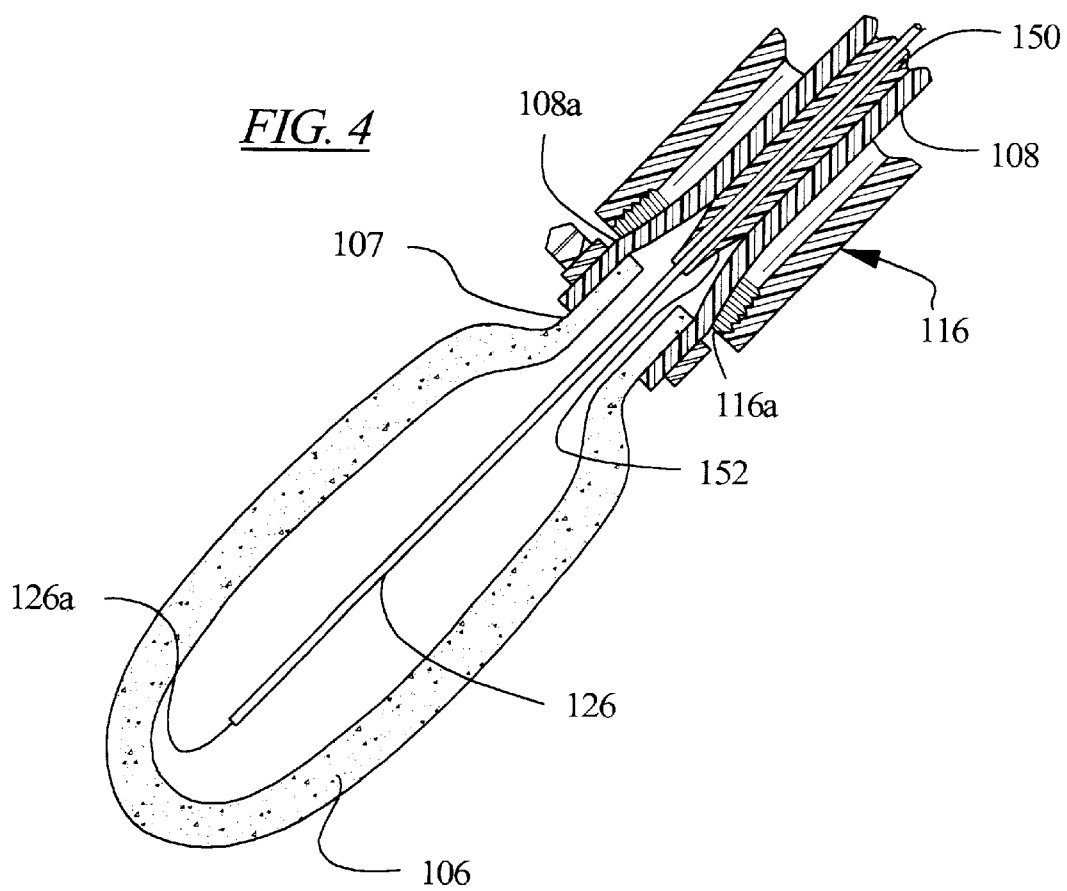
FIG. 4 is a sectional view of a portion of the apparatus of FIG. 3.

FIG. 4 illustrates the outer flexible tube 108 clamped to an outlet neck 107 of the filter 106. The neck 107 is sized such that the outer flexible tube 108 is bulged or flared outwardly at an end 108a, around the neck 107. The neck 107 of the filter preferably has an outer diameter of 13 mm and an inner diameter of 8 mm. The size of the bulged end 108a is about the size of an open end 116a of the coupling 116. Thus, the bulged end 108a when drawn against the end 116a, substantially closes the open end 116a to help keep matter out of the coupling 116 and the outer PVC sleeve 114. The inner flexible tube 126 inserts through the outer flexible tube 108 and into the filter 106. The inner flexible tube 126 is centered in position to the filter 106 at the neck 107 by a tubular fitting or insert 150, preferably plastic, having a tapered insertion end 152. The fitting has an outside diameter of 10 mm and an inside diameter of 6 mm. The fitting 150 is sized to be sufficiently loose between the outside diameter of the inner flexible tube 126 and the inside diameter of the fitting 150 to allow free flow of air past the fitting 150, through the outer flexible tube 108.

In a preliminary study, the rates at which water passively entered two cup-shaped porous ceramic filters (such as manufactured by Soil Moisture Equipment Corp., Santa Barbara, Calif.) vented to the atmosphere were evaluated. A filter was desired which allowed about 5 ml of water to enter per minute to ensure that water could be removed from inside the filter faster than its entry rate into the filter. Therefore, the speed of an in-line peristaltic pump was adjusted to keep air entering a sampling tube placed in the filter. The larger filter had a diameter of 4 cm, a length of 19 cm, a wall thickness of 0.5 cm, and a pore size of 6 $\mu$m (Soil Moisture Equipment Corp, part number 652X18-B.5M2). The smaller filter measured 2.2 cm in diameter, 6 cm in length, had a wall thickness of 0.2 cm and a pore size of 6 $\mu$m (Soil Moisture Equipment Corp. part number 655X01-B.5M2). Both filters had a saturated hydraulic conductivity of $3.11\times10^{-5}$ cm/sec. It was concluded from the preliminary study that the smaller filter was more appropriate because water entered the larger filter more quickly than desired.

In the first study, a ruminally cannulated lactating Holstein cow receiving ad libitum access to a totally mixed ration (TMR) fed twice daily and consisting of corn silage, alfalfa haylage, and a ground corn and soybean meal-based concentrate mixture (25:25:50 on a DM basis) was used. The time-integrated sampler was placed in the ventral rumen of the cow for two 36-h (with 6-h collection intervals) periods to determine the rate of ruminal fluid uptake and, in the process, the susceptibility of the filter to clogging. During this period observations were also made concerning ruminal fluid uptake during standing and lying, and to ensure that the device did not interfere with normal ruminal contractions.

In a second study, two non-lactating Holstein cows (fitted with permanent ruminal cannulas) given ad libitum access to the same TMR fed in the first study once daily were used in a split-plot design to determine the utility of the time-integrated device for obtaining ruminal fluid samples representative of the dynamic fermentation environment. Sampling was evaluated by comparing the volatile fatty acid concentrations in ruminal fluid collected by the time-integrated device with that collected using the conventional suction-strainer device. Ruminal fluid sampled by both methods was collected in four 8-h studies starting either 2 h before or 6 h after feeding. Samples were collected continuously at 1-h intervals by the time-integrated method while sampling occurred every 30 min using the suction-strainer device. The 30-min collection interval used for the suction-strainer device was necessary to determine if the time-integrated sampler provided an accurate estimate of the overall ruminal fermentation environment with respect to time.

Immediately following collection, all suction-stainer samples were placed in ice water to stop fermentation, mixed, and subsampled (50 ml) for pH and volatile fatty acids analysis. Ruminal fluid collected by the time-integrated sampler was acidified with 15 ml of 25%-metaphosphoric acid as it entered the collection vessel. The collection vessel was stored in ice water. Subsamples (50 ml) from the suction-strainer device were stabilized by the addition of 15 ml of 25%-metaphosphoric acid. All samples were filtered through four layers of cheesecloth, and centrifuged for 20 min at 20,000×g and $-15°$ C. The supernatant was transferred to two 1.5-ml micro-centrifuge tubes and frozen overnight at $-20°$ C. to precipitate soluble protein. Samples were then thawed to room temperature and centrifuged again (20 min at 20,000×g and $-15°$ C.). Volatile fatty acid concentrations in the supernatants were determined using a Vista 44 gas liquid chromatograph (Varian, Walnut Creet, Calif.) and 2-ethyl butyric acid as an internal standard.

Methods were compared using analysis of variance for a split-plot design. The model included the effects of study, method, time, method by time interaction, and study by method interaction as the error term for method. If a significant (P<0.05) F value was indicated for a main effect, then comparisons were made using Tukey's Test to detect differences among methods.

The rate of ruminal fluid uptake by the time-integrated sampler averaged 0.359±0.006 ml/min over the two 36-h periods and was unaffected (P>0.05) by time. Sampling occurred while the animal was standing and lying down. There were no visible signs of discomfort or any indication that ruminal contractions were altered. The consistency of uptake observed for the method indicated that the time-integrated sampler was not susceptible to clogging during this time period and that position of the animal (lying or standing) did not influence uptake.

Total ruminal fluid volatile fatty acid concentrations in samples collected using the time-integrated sampler did not differ (P>0.05) from those gathered using the suction-strainer device (Table 1). Molar percentage of propionate, isobutyrate, butyrate, isovalerate, and valerate in samples that began collection 2 h before feeding were similar (P>0.05) between methods, but acetate was 2.5% higher (P<0.05) in samples collected by the suction-strainer device (Table 2). Molar percentages of acetate, propionate, isobutyrte, butyrate, and isovalerate in samples that began collection 6 h post-feeding were similarly unaffected (P>0.05) by method except valerate, which was 5% higher (P<0.05) in samples collected by the suction-strainer device. Although significant, the small differences are not considered physiologically important and may represent a type I error arising because of the many comparisons made.

Although already in usable form, the device could be further developed to allow sampling under ambulatory conditions.

The device could possibly be adapted for use in human and in veterinary medicine to obtain larger fluid samples from the gastrointestinal tract via endoscopy.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

TABLE 1

Total volatile fatty acid concentrations

| Method | 2 h Before feeding[a] | 6 h Post-feeding[a] |
|---|---|---|
| Suction-strainer device, mM | 79.3 | 78.1 |
| Time-integrated device, mM | 74.0 | 73.0 |
| SEM[b] | 13.3 | 5.7 |

[a]Period starting time.
[b]Pooled standard error of the means estimated across time within an 8-h study.

TABLE 2

Volatile fatty acid pattern (moles/100 moles)

| Method | Acetate | Propionate | Isobutyrate | Butyrate | Isovalerate | Valerate |
|---|---|---|---|---|---|---|
| Period starting 2 h before feeding | | | | | | |
| Suction-strainer device | 65.4[a] | 18.7[a] | 1.3[a] | 11.5[a] | 1.6[a] | 1.5[a] |
| Time-integrated device | 63.8[b] | 19.9[a] | 1.4[a] | 11.8[a] | 1.7[a] | 1.4[a] |
| SEM[c] | .9 | .5 | .3 | .4 | .3 | .2 |
| Period starting 6 h Post-feeding | | | | | | |
| Suction-strainer device | 62.6[a] | 19.0[a] | 1.2[a] | 13.7[a] | 1.9[a] | 1.6[a] |
| Time-integrated device | 62.1[a] | 19.1[a] | 1.3[a] | 14.1[a] | 1.9[a] | 1.5[b] |
| SEM[c] | .4 | .4 | .1 | .4 | .1 | .2 |

[a,b]Means in the same column and sampling period with different superscripts differ ($P < .05$).
[c]Pooled standard error of the means estimated across time within an 8-h study.

The invention claimed is:

1. A system for sampling bodily fluid in an animal's body, comprising:
    a collection vessel;
    a cup-shaped ceramic filter adapted to be placed at a sampling site within the body of the animal;
    an inner tube flow-connected to a collection region within said ceramic filter at one end and adapted to extend out of the animal's body to a second end;
    an outer tube coaxially surrounding said inner tube and having a first open end adjacent said ceramic filter and a second end adapted to extend to an outside of the animal's body; and
    a peristaltic pump having an inlet connected to said inner tube and an outlet connectable to said collection vessel.

2. The system according to claim 1, further comprising an outer surrounding conduit surrounding said outer tube and adapted to extend from adjacent said ceramic filter to outside of the animal body, said outer conduit adapted to extend through a cannula formed through the animal body, said outer conduit attached to a cannula cover which closes said cannula.

3. The system according to claim 1, wherein said filter comprises a wall thickness of about 0.2 centimeters.

4. The system according to claim 1, wherein said filter comprises a pore size of about 6 micrometers.

5. A method for sampling bodily fluid in an animal's body comprising the steps of:
    providing a filter element having a filtering wall in fluid communication with an internal void;
    connecting the filter element to a tube for removing fluid collected in said filter element;
    inserting the filter element at a sampling site within the body of the animal and collecting fluid passing through the filtering wall within the internal void of the filter element; and
    removing fluid collected in said internal void by a pump while maintaining pressure within the internal void at near atmospheric pressure.

6. The method according to claim 5, wherein said step of removing fluid is further defined in that a second tube is connected to said filter element, said second tube exposing an inside of said filter element to atmospheric air from outside said animal's body.

7. A sampling apparatus for sampling fluids inside an animal's body comprising:
    a peristaltic pump;
    a filter element adapted to be placed inside the body of the animal and comprising a filtering media defining an outside surface and an inside surface that defines an enclosed volume;
    a first tube flow-connected to said enclosed volume at one end and open at an opposite end; and
    a second tube flow-connected to said enclosed volume at one end and to a suction of said peristaltic pump at an opposite end.

8. The sampling apparatus according to claim 7, wherein said second tube has a smaller diameter than said first tube and is fit coaxially within said first tube.

9. The sampling apparatus according to claim 7 further comprising an outer conduit connected to said filter element at one end and connected to a cannula cover at a position on said outer conduit spaced from said filter element, said first and second tubes fit within said outer conduit.

10. The sampling apparatus according to claim 7, wherein said filter element comprises a filtering media wall thickness of about 0.2 centimeters.

11. The sampling apparatus according to claim 7, wherein said filter element filtering media comprises a pore size of about 6 micrometers.

12. A sampling apparatus for sampling fluids inside an animal's body comprising:
    a peristaltic pump;
    a filter element comprising a filtering media defining an outside surface and an inside surface that defines an enclosed volume;
    a first tube flow-connected to said enclosed volume at one end and open at an opposite end;
    a second tube flow-connected to said enclosed volume at one end and to said peristaltic pump at an opposite end; and
    an outer conduit connected to said filter element at one end and connected to a cannula cover at a position on said outer conduit spaced from said filter element, said first and second tubes fit within said outer conduit.

13. A sampling apparatus for sampling fluids inside an animal's body, comprising:

a suction device having an inlet for drawing fluid;

a filter element adapted to be placed inside the body of the animal and having a porous filtering wall and an enclosed void at least partly defined by said porous filtering wall;

a first tube flow-connected to said void at one end and open at an opposite end, said tube adapted for said opposite end to be outside the body of the animal; and a second tube flow-connected to said void at one end to said inlet of said suction device at an opposite end.

14. The sampling apparatus according to claim 13, wherein said suction device comprises a pump.

15. The sampling apparatus according to claim 13, wherein said filter element comprises a wall of porous material surrounding said internal void.

16. The sampling apparatus according to claim 13, wherein said second tube has a smaller diameter than said first tube and is fit coaxially within said first tube.

17. The sampling apparatus according to claim 13, further comprising an outer conduit connected to said filter element at one end and connected to a cannula cover at a position on said outer conduit spaced from said filter element, said first and second tubes fit within said outer conduit.

18. The sampling apparatus according to claim 13, wherein said suction device comprises a peristaltic pump;

wherein said filter element comprises a cup-shaped wall of porous materials surrounding said internal void;

wherein said second tube has a smaller diameter than said first tube and is fit coaxially within said first tube; and further comprising an outer conduit and a cannula cover adapted to seal an opening to the body of the animal, said outer conduit connected to said filter element at one end and connected to said cannula cover at a position on said outer conduit spaced from said filter element, said first and second tubes fit within said outer conduit.

19. The sampling apparatus according to claim 18, wherein said filter element comprises a ceramic filter.

20. The sampling apparatus according to claim 18, wherein said filter element comprises a ceramic filter having a pore size of about 6 micrometers.

\* \* \* \* \*

UNITED STATES PATENT AND TRADEMARK OFFICE
CERTIFICATE OF CORRECTION

PATENT NO.   : 6,533,734 B1
DATED        : March 18, 2003
INVENTOR(S)  : Corley et al.

It is certified that error appears in the above-identified patent and that said Letters Patent is hereby corrected as shown below:

Column 1,
Lines 6-7, replace "and the Government has certain rights in the invention" with
-- under Contract Number HATCH RRF 35-309 NE-132 awarded by the United States Department of Agriculture (USDA). The Government has certain rights in the invention --.

Signed and Sealed this

Second Day of September, 2003

JAMES E. ROGAN
*Director of the United States Patent and Trademark Office*